(12) United States Patent
Weber et al.

(10) Patent No.: US 8,834,560 B2
(45) Date of Patent: Sep. 16, 2014

(54) ENDOPROSTHESIS

(75) Inventors: Jan Weber, Maastricht (NL); Liliana Atanasoska, Minneapolis, MN (US); James Lee Shippy, III, Wilmington, NC (US); Torsten Scheuermann, Munich (DE); Daniel J. Gregorich, Plymouth, MN (US); Michael P. Meyer, Richfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 461 days.

(21) Appl. No.: 13/051,496

(22) Filed: Mar. 18, 2011

(65) Prior Publication Data
US 2011/0245905 A1  Oct. 6, 2011

Related U.S. Application Data

(60) Provisional application No. 61/321,393, filed on Apr. 6, 2010.

(51) Int. Cl.
*A61F 2/06* (2013.01)
*A61L 31/14* (2006.01)
*A61L 31/08* (2006.01)
*A61L 31/06* (2006.01)
*A61L 31/16* (2006.01)
*A61L 31/10* (2006.01)
*A61L 31/04* (2006.01)

(52) U.S. Cl.
CPC ............. *A61L 31/088* (2013.01); *A61L 31/148* (2013.01); *A61L 31/06* (2013.01); *A61L 31/16* (2013.01); *A61L 31/10* (2013.01); *A61L 31/044* (2013.01)

USPC ........................................................ 623/1.38

(58) Field of Classification Search
USPC ............................................... 623/1.15–1.48
See application file for complete search history.

(56) References Cited

U.S. PATENT DOCUMENTS

| | | | |
|---|---|---|---|
| 5,091,205 A | 2/1992 | Fan |
| 5,171,607 A | 12/1992 | Cumbo |
| 5,378,146 A | 1/1995 | Sterrett |
| 5,649,977 A | 7/1997 | Campbell |
| 5,733,925 A | 3/1998 | Kunz et al. |
| 5,891,192 A | 4/1999 | Murayama et al. |
| 5,962,136 A | 10/1999 | Dewez et al. |

(Continued)

FOREIGN PATENT DOCUMENTS

| | | |
|---|---|---|
| CA | 2561667 | 10/2005 |
| EP | 0824900 | 2/1998 |

(Continued)

OTHER PUBLICATIONS

"Iron Corrosion Products", Corrosion Doctors, 4 pages, (2004), (http://corrosion-doctors.org/Experiments/iron-products.htm).

(Continued)

*Primary Examiner* — Suzette J Gherbi
(74) *Attorney, Agent, or Firm* — Fish & Richardson P.C.

(57) ABSTRACT

Among other things, a bio-erodible implantable endoprosthesis comprises a member that includes (a) a core having a surface, and (b) a bio-erodible metal on a least a portion of the surface of the core, wherein the bio-erodible metal erodes more slowly than the core and includes openings through which physiological fluids can access the core upon implantation.

24 Claims, 8 Drawing Sheets

(56) References Cited

U.S. PATENT DOCUMENTS

| | | |
|---|---|---|
| 6,290,721 B1 | 9/2001 | Heath |
| 6,416,820 B1 | 7/2002 | Yamada et al. |
| 6,517,888 B1 | 2/2003 | Weber |
| 6,761,736 B1 | 7/2004 | Woo et al. |
| 7,727,273 B2 | 6/2010 | Stinson et al. |
| 7,967,855 B2 * | 6/2011 | Furst et al. ............... 623/1.42 |
| 8,524,148 B2 * | 9/2013 | Shrivastava et al. ........ 419/66 |
| 2001/0044651 A1 | 11/2001 | Steinke et al. |
| 2002/0144757 A1 | 10/2002 | Craig et al. |
| 2003/0009233 A1 | 1/2003 | Blinn et al. |
| 2003/0018380 A1 | 1/2003 | Craig et al. |
| 2003/0077200 A1 | 4/2003 | Craig et al. |
| 2003/0104028 A1 | 6/2003 | Hossainy et al. |
| 2003/0153971 A1 | 8/2003 | Chandrasekaran |
| 2003/0225450 A1 | 12/2003 | Shulze et al. |
| 2004/0106994 A1 | 6/2004 | De Maeztus et al. |
| 2004/0143317 A1 | 7/2004 | Stinson et al. |
| 2004/0181276 A1 | 9/2004 | Brown et al. |
| 2004/0261702 A1 | 12/2004 | Grabowy et al. |
| 2005/0019265 A1 | 1/2005 | Hammer et al. |
| 2005/0070990 A1 | 3/2005 | Stinson |
| 2005/0079201 A1 | 4/2005 | Rathenow et al. |
| 2005/0197687 A1 | 9/2005 | Molaei et al. |
| 2005/0209680 A1 * | 9/2005 | Gale et al. ............... 623/1.15 |
| 2005/0216074 A1 | 9/2005 | Sahatjian et al. |
| 2006/0038027 A1 | 2/2006 | O'Connor et al. |
| 2006/0079863 A1 | 4/2006 | Burgmeier et al. |
| 2006/0127443 A1 | 6/2006 | Helmus |
| 2006/0129215 A1 | 6/2006 | Helmus et al. |
| 2007/0038176 A1 | 2/2007 | Weber et al. |
| 2008/0069858 A1 | 3/2008 | Weber |
| 2008/0147177 A1 | 6/2008 | Scheuermann et al. |
| 2008/0195170 A1 | 8/2008 | Asgari |
| 2009/0131540 A1 * | 5/2009 | Hiromoto et al. ........... 514/769 |
| 2010/0256728 A1 * | 10/2010 | Rea Peterson ............ 623/1.13 |
| 2011/0077732 A1 * | 3/2011 | Bayer et al. ............... 623/1.44 |
| 2011/0178593 A1 * | 7/2011 | Klocke et al. ............. 623/1.42 |
| 2011/0238155 A1 * | 9/2011 | Wang ....................... 623/1.15 |
| 2011/0264190 A1 * | 10/2011 | McClain et al. ........... 623/1.11 |
| 2011/0282428 A1 * | 11/2011 | Meyer et al. ............... 623/1.15 |
| 2011/0282430 A1 * | 11/2011 | Atanasoska et al. ........ 623/1.15 |
| 2012/0158126 A1 * | 6/2012 | Klocke et al. ............. 623/1.42 |

FOREIGN PATENT DOCUMENTS

| | | |
|---|---|---|
| EP | 1754684 | 2/2007 |
| EP | 19980223 | 10/2008 |
| WO | WO 01/80920 | 11/2001 |
| WO | WO 2006/061598 | 6/2006 |
| WO | 2006/086624 | 8/2006 |
| WO | WO 2008/034048 | 3/2008 |
| WO | 2008/118606 | 10/2008 |
| WO | 2009/059081 | 5/2009 |

OTHER PUBLICATIONS

"Rust Chemisty", Corrosion Doctors, 2 pages, (2004), (http://corrosion-doctors.org/Experiments/rust-chemistry.htm).

Berry et al., "Functionalisation of magnetic nanoparticles for applications in biomedicine," Journal of Physics D: Applied Physics, vol. 36, pp. R198-R206, (2003).

Bet et al., "Characterization of Polyanionic Collagen Prepared by Selective Hydrolysis of Asparagine and Glutamine Carboxyamide Side Chains," Biomacromolecules, vol. 2, pp. 1074-1079, (2001).

Bronstein et al., "Complexes of Polyelectrolyte Gels with Oppositely Charged Surfactants: Interaction with Metal Ions and Metal Nanoparticle Formation," Langmuir, vol. 14, pp. 252-259, (1998).

Buchaim et al., "Biocompatibility of anionic collagen matrices and its influence on the orientation of cellular growth," Brazilian Oral Research, vol. 10, No. 3, pp. 12-20, Jul. 2007.

Cornwell et al., "Fibroblast Migration on Discrete Self-Assembled Collagen Threads," Materials Research Society Symposia Proceedings, vol. EXS-1, pp. F3.11.1-F3.11.3, (2004).

Day, Nanometal-Polymer Hybrid, Advanced Materials and Processes, pp. 25-27, Apr. 2008.

Dinderman et al., "Electroless Plating of Iron onto Cellulose Fibers," Chem. Mater., vol. 18, pp. 4361-4368, (2006).

Gibson et al., "Synthesis of a Low Molecular Weight Collagen by Chondrocytes from the Presumptive Calcification Region of the Embryonic Chick Sterna: The Influence of Culture with Collagen Gels," Journal of Cell Biology, vol. 99, 208-216, Jul. 1, 1984.

Goissis et al., "Anionic Collagen for Biomedical Application," 10th international symposium on electrets, pp. 229-232, (1999).

Goissis et al., "Surface tension control of collagen biomaterials by the selective hydrolysis of internal carboxyamides of the protein matrix," Revista Brasileira de Engenharia Biomedica, vol. 15, No. 1-2, pp. 55-61, Jan. 1999.

Gupta et al., "Synthesis and surface engineering of iron oxide nanoparticles for biomedical applications," Biomaterials vol. 26, pp. 3995-4021, (2005).

Hershko et al., "Evaluation of iron-chelating agents in an in vivo system: potential usefulness of EHPG, a powerful iron-chelating drug," British Journal of Haematology, vol. 51, pp. 251-260, (1982).

Lai et al., "The rheological behavior of collagen dispersion/poly(vinyl alcohol) blends," Korean-Australian Rheology Journal, vol. 19, No. 2, pp. 81-88, Aug. 2007.

Lima et al., "DC conductivity and dielectric permittivity of collagen-chitosan films," Materials Chemistry and Physics, vol. 99, pp. 284-288, (2006).

Lin et al., "In situ synthesis of bone-like apatite/collagen nano-composite at low temperature," Materials Letters, vol. 58, pp. 3569-3572, (2004).

Lou et al., "Swelling Behavior and Mechanical Properties of Chemically Cross-Linked Gelatin Gels for Biomedical Use," Journal of Biomaterials Applications, vol. 14, pp. 184-191, Oct. 1999.

McLean et al., "Metal-Binding Characteristics of the Gamma-Glutamyl Capsular Polymer of *Bacillus licheniformis* ATCC 9945," Applied and Environmental Microbiology, vol. 56, No. 12, pp. 3671-3677, Dec. 1990.

Nordlander et al., "Iron 1995," Coordination Chemistry Reviews, vol. 172, pp. 3-97, (1998).

Phenrat et al., "Stabilization of aqueous nanoscale zerovalent iron dispersions by anionic polyelectrolytes: adsorbed anionic polyelectrolyte layer properties and their effect on aggregation and sedimentation," J. Nanopart. Res. vol. 10, pp. 795-814, (2008).

Roeder et al., "Tensile Mechanical Properties of Three-Dimensional Type I Collagen Extracellular Matrices With Varied Microstructure," Transactions of the ASME, vol. 124, pp. 214-222, Apr. 2002.

Rosenblatt et al., "De novo designed cyclic-peptide heme complexes," PNAS, vol. 100, No. 23, pp. 13140-13145, Nov. 11, 2003.

Santos et al., "Low-cost Processing Technology for the Synthesis of Calcium Phosphates/Collagen Biocomposites for Potential Bone Tissue Engineering Applications," Materials Research, vol. 10, No. 4, pp. 431-436, (2007).

Sarin et al., "Iron Corrosion Scales: Model for Scale Growth, Iron Release, and Colored Water Formation," Journal of Envionmental Engineering, vol. 130, No. 4, pp. 364-373, Apr. 1, 2004.

Schetsky, "Shape Memory Alloys", Encyclopedia of Chemical Technology (3rd ed.), John Wiley & Sons, vol. 20, pp. 726-736, (1982).

Seth et al., "Binding of iron by chicken muscle protein digests: the size of the iron-binding peptides," Journal of the Science of Food and Agriculture, vol. 80, pp. 1595-1600, (2000).

Shears et al., "Iron complexation to carboxyl groups in a bovine serum albumin digest", International Journal of Food Science & Technology, vol. 22, Issue 3, pp. 265-272, Jul. 1987.

Wallace et al., "Collagen gel systems for sustained delivery and tissue engineering," Advanced Drug Delivery Reviews, vol. 55, pp. 1631-1649, (2003).

Wolf et al., "Characterizations of Collagen Fibers for Biodegradable Films Production," IUFoST World Congress: 13th World Congress of Food Science & Technology, Issue 2006, 2 pages, (2006).

Wood et al., "The Formation of Fibrils from Collagen Solutions," Biochem. J., vol. 75, pp. 588-598, (1960).

Yu et al., "Characterization of iron complexes supported on polymer and their catalytic activity in butadiene polymerization," Chinese Journal of Polymer Science vol. 8, No. 3, pp. 247-252, (1990).

(56) References Cited

OTHER PUBLICATIONS

Zeugolis et al., "Extruded Collagen-Polyethylene Glycol Fibers for Tissue Engineering Applications," Journal of Biomedical Materials Research Part B: Applied Biomaterials, vol. 85B, pp. 343-352, (2008).

Invitation of Pay Additional Fees, mailed on Jun. 22, 2011, by the WIPO in the related PCT application PCT/US2011/029002, filed on Mar. 18, 2011.

International Search Report and Written Opinion issued on Aug. 26, 2011, in the PCT application PCT/US2011/029002, filed on Mar. 18, 2011.

International Preliminary Report on Patentability & Written Opinion issued on Oct. 18, 2012, in the PCT application No. PCT/US2011/029002; 12 pages.

Amanatides et al., "Electrical and optical properties of CHJH2 RF plasmas for diamond-like thin film deposition", Diamond & Related Materials, vol. 14, (2005), 292-295.

Ashfold et al., "Pulsed laser ablation and deposition of thin films" Chem. Soc. Rev., vol. 33, (2004), 23-31.

Calcagno et al., "Structural modification of polymer films by ion irradiation", Nuclear Instruments and Methods in Physics Research. vol. 865, (1992), 413-422.

Chen et al., "Blood compatibility and $sp^3/sp^2$ contents of diamond-like carbon (DLC) synthesized by plasma immersion ion implantation-deposition", Surface and Coatings Technology, vol. 156 (2002) pp. 289-294.

Choi et al., "Synthesis and Characterization of Diamond-Like Carbon Protective AR Coating", Journal of the Korean Physical Society, vol. 45, Dec. 2004, S864.

Chow et al., "Nanostructured Films and Coating by Evaporation, Sputtering, Thermal Spraying, Electro-and Electroless Deposition", Handbook of Nanophase and Nanostructured Materials, vol. 1, Synthesis, Chapter 9, 246-272.

Chu, "Recent developments and applications of plasma immersion ion implantation", J. Vac. Sci. Technol., vol. 822, No. 1, Jan./Feb. 2004, 289-296.

FreeOnlineDictionary, "Aperture," retrieved Oct. 9, 2009, http://www.thefreedictionary.com/aperture, 1 page.

Fu et al., "Effects of mesh-assisted carbon plasma immersion ion implantation on the surface properties of insulating silicon carbide ceramics", J. Vac. Sci. Technol, vol. A22, No. 2, Mar./Apr. 2004, 356-360.

Fu et al., "Influence of thickness and dielectric properties on implantation efficacy in plasma immersion ion implantation of insulators", Journal of Applied Physics, vol. 95, No. 7, Apr. 1, 2004, 3319-3323.

Fulton, "Ion-Assisted Filtered Cathodic Arc Deposition (IFCAD) System for Volume Production of Thin-Film Coatings", Society of Vacuum Coalers, 42nd Annual Technical Conference Proceedings (1999).

Han et al., "Electron injection enhancement by diamond-like carbon film in organic electroluminescence devices", Thin Solid Films, vol. 420-421, (2002), 190-194.

Hanley et al., "The growth and modification of materials via ion-surface processing", Surface Science, vol. 500, (2002), 500-522.

He et al., "Optical properties of diamond-like carbon synthesized by plasma immersion ion processing", J. Vac. Sci. Technol., vol. 817, No. 2, Mar./Apr. 1999,. 822-827.

Kanda et al., "Characterization of Hard Diamond-Like Carbon Films Formed by Ar Gas Cluster Ion Beam-Assisted Fullerene Deposition", Jpn. J. Appln. Phys., vol. 41, (2002), pp. 4295-4298.

Kitagawa et al., "Near-Edge X-Ray Absorption Fine Structure Study for Optimization of Hard Diamond-Like Carbon Film Formation with Ar Cluster Ion Beam", Jpn. J. Appln. Phys., vol. 42, (2003), 3971-3975.

Kitagawa et al., "Optimum Incident Angle of Ar Cluster Ion Beam for Superhard Carbon Film Deposition", Japanese Journal of Applied Physics, vol. 43, No. 6B, (2004), 3955-3958.

Kitagawa et al., "Study of Ar Cluster Ion Incident Angle for Super Hard Diamond Like Carbon Film Deposition", USVOR Activity report, (2003), B 1 BL8, 2 pgs.

Kondyurin et al., "Plasma immersion ion implantation of polyethylene", Vacuum, vol. 64 (2002), 105-111.

Konig et al., "Nanoprocessing with nanojoule near-infrared femtosecond laser pulses", Medical Laser Application, vol. 20, (2005), 169-184.

Kostov et al., "Two Dimensional Computer Simulation of Plasma Immersion Ion Implantation", Brazilian Journal of Physics, vol. 34, No. 48, Dec. 2004, 1689-1695.

Leng et al., "Mechanical properties and platelet adhesion behavior of diamond-like carbon films synthesized by pulsed vacuum arc plasma deposition", Surface Science, vol. 531, (2003), 177-184.

Lippert et al., "Chemical and Spectroscopic Aspects of Polymer Ablation: Special Features and Novel Directions", Chem. Rev., vol. 103, (2003), pp. 453-485.

Meijer et al., "Laser Machining by Short and Ultrashort Pulses, State of the Art and New Opportunities in the Age of the Photons", Annals of the CIRP, vol. 5112, (2002), 531-550.

Neves et al., "The morphology, mechanical properties and ageing behavior of porous injection molded starch-based blends for tissue engineering scaffolding", Materials Science and Engineering, vol. C25, (2005),. 195-200.

Orloff et al., "Biodegradable implant strategies for inhibition of restenosis," Advanced Drug Delivery Reviews, vol. 24, (1997) pp. 3-9.

Pelletier et al., "Plasma-based ion implantation and deposition: A review of physics, technology, and applications", Lawrence Berkeley and National Laboratory, May 16, 2005, 1-68.

Piazza et al., "Protective diamond-like carbon coatings for future optical storage disks", Diamond & Related Materials, vol. 14, (2005), 994-999.

Azom.com, "PVD Materials—Materials Available for Physical Vapour Deposition (PVD) from Williams Advanced Materials," retrieved on Apr. 28, 2006, www.azom.com/details.asp?ArticleID=2940, 8 pages.

Rossi et al., "Pulsed Power Modulators for Surface Treatment by Plasma Immersion Ion Implantation", Brazilian Journal of Physics, vol. 34, No. 48, Dec. 2004, 1565-1571.

Sofield et al., "Ion beam modification of polymers", Nuclear Instruments and Methods in Physics Research, vol. B67, (1992), 432-437.

Thompson et al., "Tuning compliance of nanoscale polyeletrolyte multilayers to modulate cell adhesion", Biomaterials, vol. 26, (2005), 6836-6845.

Tollon, "Fabrication of coated biodegradable polymer scaffolds and their effects on murin embryonic stem cells," 2005, 7 pages.

Tonosaki et al., "Nano-identation testing for plasma-based ion-implanted surface of plastics", Surface and Coatings Technology, vol. 136 (2001), 249-251.

Zilberman et al., "Protein-loaded bioresorbable fibers and expandable stents: Mechanical Properties and protein release," Journal of Biomedical Materials Research. Part B: Applied Biomaterials, vol. 69B, pp. 1-10 Aug. 14, 2003.

* cited by examiner

ENDOPROSTHESIS

CROSS-REFERENCE TO RELATED APPLICATION

This application claims priority under 35 USC §119(e) to U.S. Provisional Patent Application Ser. No. 61/321,393, filed on Apr. 6, 2010, the entire contents of which are hereby incorporated by reference.

TECHNICAL FIELD

This invention relates to endoprostheses.

BACKGROUND

The body includes various passageways such as arteries, other blood vessels and other body lumens. These passageways sometimes become occluded or weakened. For example, the passageways can be occluded by a tumor, restricted by plaque, or weakened by an aneurysm. When this occurs, the passageway can be reopened or reinforced with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, e.g., so that it can contact the walls of the lumen. Stent delivery is further discussed in Heath, U.S. Pat. No. 6,290,721.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn from the lumen.

SUMMARY

In one aspect, the invention features a bio-erodible implantable endoprosthesis comprising a member that includes (a) a core having a surface, and (b) a bio-erodible metal on a least a portion of the surface of the core, wherein the bio-erodible metal erodes more slowly than the core and includes openings through which physiological fluids can access the core upon implantation.

Embodiments may include any one or more of the following features. The core comprises a bio-erodible polymer. The bio-erodible polymer is PLA, PLGA, or a combination thereof. The core comprises a collagen. The core includes a drug. The core includes radiopaque particles. The bio-erodible metal comprises iron or an alloy thereof. The bio-erodible metal comprises magnesium or an alloy thereof. The bio-erodible metal comprises a plurality of pores through which physiological fluids can access the core upon implantation. The pores are micron-sized pores having a diameter of about 1 micron to about 20 microns. The bio-erodible metal is provided with channels through which physiological fluids can access the core upon implantation. The bio-erodible metal is in the form of a mesh. The bio-erodible metal has a thickness of about 20 microns to about 40 microns. The member is a strut. The endoprosthesis is a stent.

In another aspect, the invention features a bio-erodible endoprosthesis comprising radially expandable members each including a metal shell covering at least a portion of a core that is mechanically less strong than the metal shell to provide radial mechanical strength when the member is expanded, and longitudinal connectors each connecting two radially expandable members along a longitudinal axis of the endoprosthesis. Each longitudinal connector can include the core without the metal shell to provide flexibility along the longitudinal axis.

In another aspect, the invention features a bio-erodible implantable endoprosthesis comprising a member that includes (a) a hollow core, (b) a porous bio-erodible metal surrounding the core and having a surface, wherein the density of the porous bio-erodible metal decreases in the thickness direction from the surface to the core, and (c) a bio-erodible layer covering at least a portion of the surface of the bio-erodible metal that provides openings through which physiological fluids can access the porous bio-erodible metal, the core, or both upon implantation.

Embodiments may include any one or more of the following features. The bio-erodible layer comprises a bio-erodible polymer. The bio-erodible polymer is PLA, PLGA, or a combination thereof. The bio-erodible polymer includes electroconductive particles. The electroconductive particles comprises electroconductive polymer particles. The porosity of the porous bio-erodible metal increases in the thickness direction from the surface to the core. The porous bio-erodible metal has a thickness of about 30 microns and the hollow core has a diameter of about 60 microns. The bio-erodible metal includes a channel in communication with the hollow core and covered by the bio-erodible layer. The bio-erodible layer is less erodible than the bio-erodible metal. The bio-erodible layer includes a drug. The bio-erodible layer is porous. The bio-erodible layer is provided with channels. The core includes radiopaque particles. The bio-erodible metal comprises iron or an alloy thereof. The bio-erodible metal comprises magnesium or an alloy thereof. The bio-erodible metal pores are nano-sized pores. The member is a strut. The member is a connector. The endoprosthesis is a stent.

In another aspect, the invention features a method of making an endoprosthesis. The method comprises depositing a first bio-erodible material conformally about a bio-erodible substrate; creating a channel through the first bio-erodible material to expose a portion of the bio-erodible substrate; removing the bio-erodible substrate through the channel; and depositing a second bio-erodible material on the first bio-erodible material and covering an opening of the channel, the second bio-erodible material being less erodible than the first bio-erodible material.

Embodiments may include any one or more of the following features. The first bio-erodible material comprises a nanoporous metal network. The first bio-erodible material is deposited using a nano-cluster deposition system. The first bio-erodible material is deposited at a deposition rate of about 1 angstrom to about 10 angstroms per second. The bio-erodible substrate comprises a bio-erodible polymer. The bio-erodible substrate is formed by micro-molding. The channel is created by laser ablation. The bio-erodible substrate is removed by calcination, plasma etching, or chemical dissolution. The second bio-erodible material comprises a bio-erodible polymer. The second bio-erodible material is deposited by spraying, dip coating, or sputtering. The second bio-erodible material has a smaller thickness over the opening of the channel than the thickness of the second bio-erodible material on the first bio-erodible material. The method also includes corroding the second bio-erodible material to uncover the opening of the channel when the second biodegradable material is in contact with a body fluid. The method also includes causing the body fluid to contact the first bio-erodible material through the channel and corrode the first bio-erodible material.

In another aspect, the invention features a bio-erodible implantable endoprosthesis comprising a member that includes (a) a bio-erodible polymer core having a surface, (b) a porous bio-erodible iron layer on a least a portion of the surface of the core, and (c) iron oxide particles in the core. The bio-erodible polymer comprises a collagen. The collagen is anionic or neutral. The core includes a drug.

In another aspect, the invention features a method of making an endoprosthesis. The method comprises forming a bio-erodible metal shell about a collagen core, the bio-erodible shell including openings through which a body fluid can reach the collagen core; corroding the bio-erodible metal shell to produce an insoluble metal compound particle in the presence of the body fluid; and incorporating the insoluble metal compound particle into the collagen core to increase a mechanical strength of the collagen core. The method can also include corroding the bio-erodible metal shell and the collagen to produce a soluble metal compound in the presence of the body fluid. The bio-erodible metal can include iron and the insoluble metal compound comprises iron oxide.

In another aspect, the invention features a bio-erodible endoprosthesis comprising a member that includes a shell. The shell comprises a first bio-erodible material and encapsulating a core comprising a second bio-erodible material, the first bio-erodible material being less corrodible than the second bio-erodible material.

Embodiments may include any one or more of the following advantages. A stent is provided with advantageous mechanical properties, biodegradability, and drug delivery. The stent can include a composite made of a metal, e.g., a biodegradable metal iron or magnesium, and a polymer, e.g., a biodegradable polymer PLGA or PLA. In particular, the stent can include inner core of a different material and/or a different density than a material radially surrounding the core. In one embodiment, the strut of the stent can have an outer polymer layer, an inner porous metal layer, and a hollow interior. The porous metal layer can be in the form of a foam and can provide substantially the same mechanical strength as a bulk metal layer having the same dimensions. The porous metal layer can degrade faster and have a smaller total mass than the bulk metal layer. The degradation of the porous metal layer can produce a less amount of the metallic material in the body of a user than the bulk metal layer. The polymer layer can provide more stiffness to the stent than the porous metal layer and can degrade more slowly than the porous metal layer. The porous metal layer can have a mass density increasing from the hollow interior towards the polymer layer, for example, continuously, to reinforce the stiffness of the polymer layer. The stent can degrade inside-out by including a pathway for a body fluid to reach into the hollow interior and corrode the porous metal layer. The desired mechanical strength provided by the polymer layer sustains during the corrosion for at least about 30 to 90 days. In another embodiment, the strut of the stent can have an outer metal layer and an inner polymer matrix. The outer metal layer can provide the mechanical strength to the stent for a desired period of time and the inner polymer matrix degrades fast after the outer layer degrades away after the period of time. The polymer matrix can also include a metal or metal oxide, e.g., in the form of particles or fibers, to provide additional mechanical strength to the stent. The polymer can be PLGA, PLA, or collagen. The metal or metal oxide in the polymer matrix can be iron or magnesium based. The polymer matrix can carry a drug that elutes after pores are formed in the outer metal layer by corrosion. The outer metal layer can also includes premade pores, for example, by laser ablation so that the drug in the polymer matrix can elute at the beginning of the use. The outer metal layer can be in the form of a mesh. The body fluid can react with the collagen in the polymer matrix the metal in the outer metal layer to provide metal complexations to be included into the collagen in vitro to provide additional mechanical strength.

DETAILED DESCRIPTION

Figure 1A:
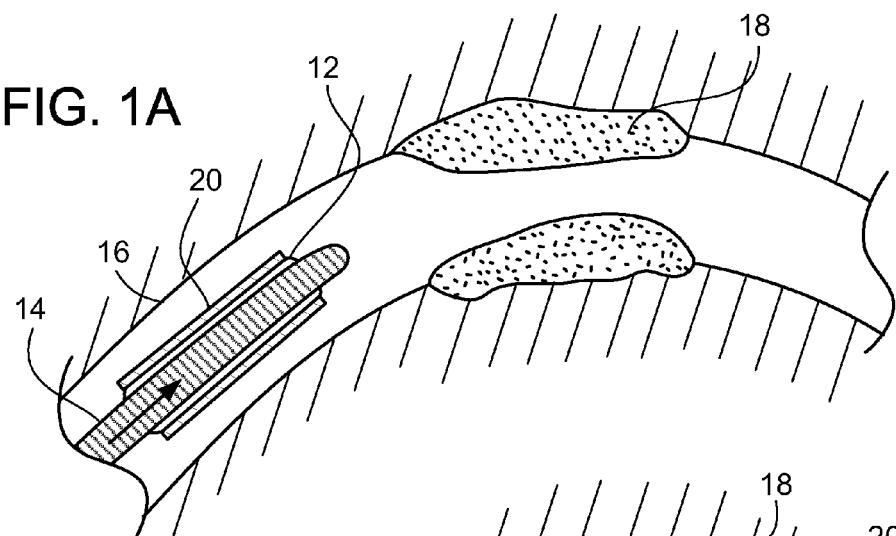
FIGS. 1A-1C are longitudinal cross-sectional views, illustrating delivery of a stent in a collapsed state, expansion of the stent, and deployment of the stent.
Figure 1B:
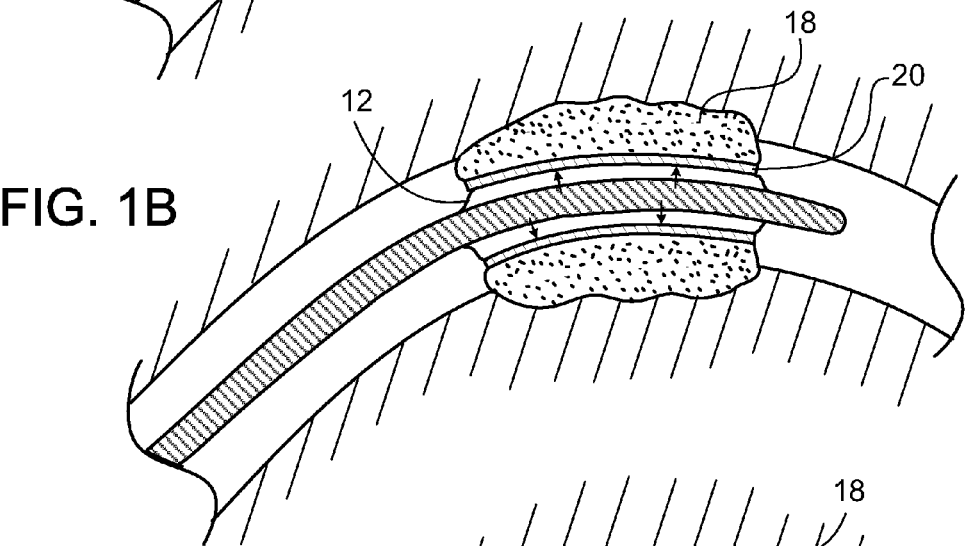
Figure 1C:
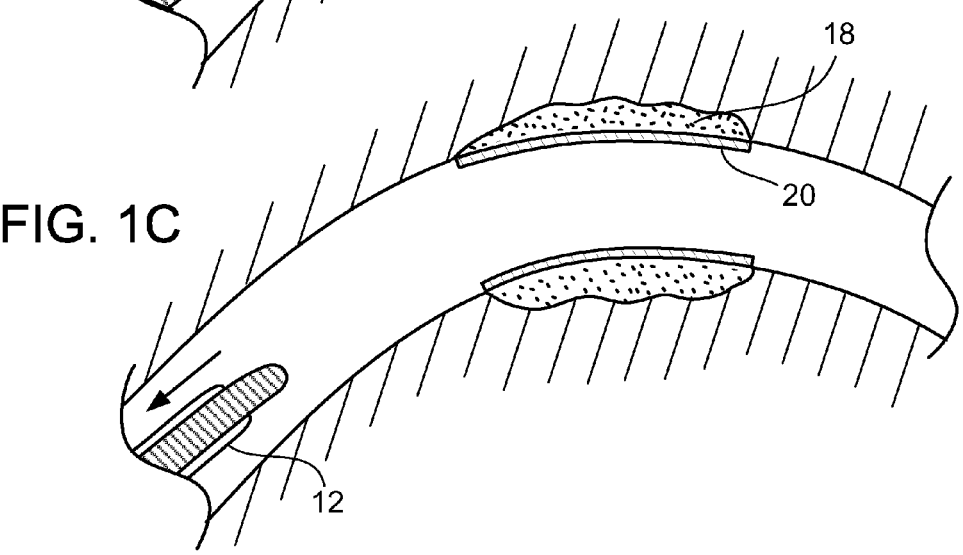

Referring to FIGS. 1A-1C, a stent 20 is placed over a balloon 12 carried near a distal end of a catheter 14, and is directed through the lumen 16 (FIG. 1A) until the portion carrying the balloon and stent reaches the region of an occlusion 18. The stent 20 is then radially expanded by inflating the balloon 12 and compressed against the vessel wall with the result that occlusion 18 is compressed, and the vessel wall surrounding it undergoes a radial expansion (FIG. 1B). The pressure is then released from the balloon and the catheter is withdrawn from the vessel (FIG. 1C).

Figure 2:
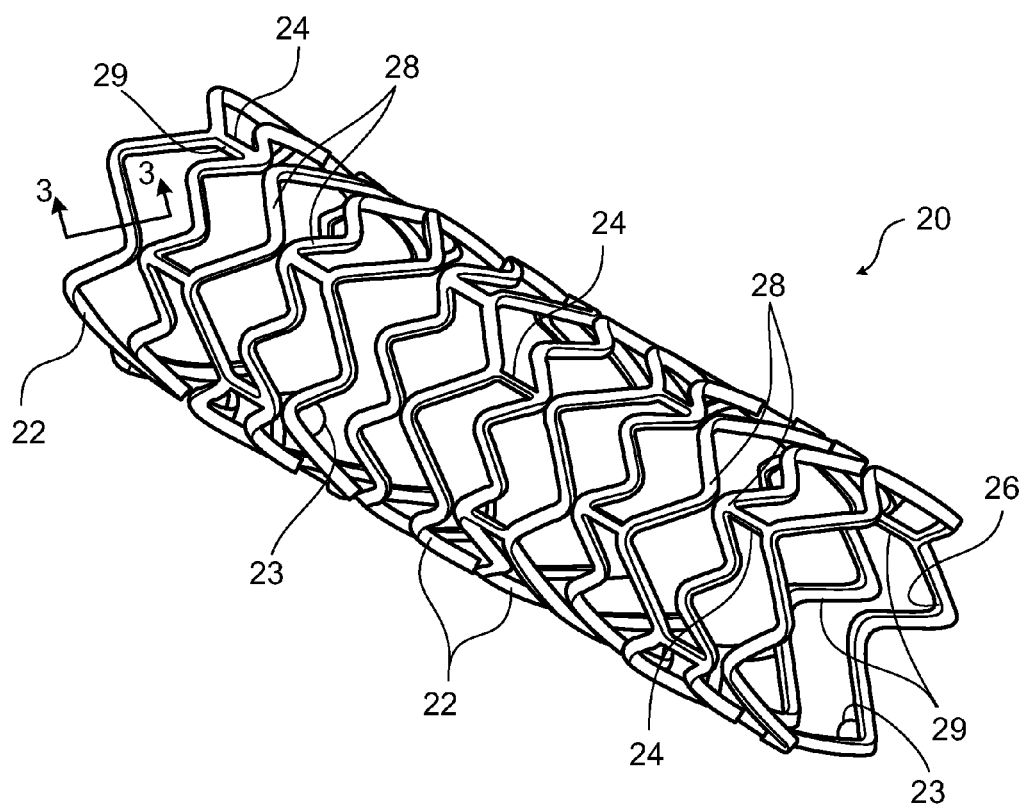
FIG. 2 is a perspective view of a stent.

Referring to FIG. 2, an expandable stent 20 can have a stent body having the form of a tubular member defined by a plurality of bands 22 and a plurality of connectors 24 that extend between and connect adjacent bands. During use, bands 22 can be expanded from an initial, smaller diameter to a larger diameter to contact stent 20 against a wall of a vessel, thereby maintaining the patency of the vessel. Connectors 24 can provide stent 20 with flexibility and conformability that allow the stent to adapt to the contours of the vessel. One or more bands 22 form acute angles 23. The angle 23 increases upon expansion of the stent. Stent body 20, bands 22 and connectors 24 can have a luminal surface 26, an abluminal surface 28, and a sidewall surface 29. In embodiments, the bands and/or connectors, have a width, W, and a thickness, T, of about 50 to 150 microns.

The stent 20 can be a biodegradable stent that degrades after being delivered into a body lumen and being in contact with a body lumen. The bands 22 and the connectors 24 can include a biodegradable material, for example, a biodegradable polymer, such as polylactic acid (PLA), poly(lactic-co-glycolic acid) (PLGA), or polyelectrolyte complexes such as heparin\chitosan, carboxymethyl cellulose, and aminoalkyl methacrylate copolymer, a biodegradable metal, such as iron, iron alloy, tungsten, tungsten alloy, magnesium, magnesium alloy, a biodegradable metal oxide, such as magnesium oxide, calcium oxide, or other materials, such as collagen. In some embodiments, the stent wall includes a combination of materials, such as a metal and a polymer, arranged to provide advantageous mechanical properties, biodegradability, and drug delivery. In some embodiments, the volume of the stent material included in the stent 20 is selected, for example, minimized, so that a limited, e.g., minimal, amount of degraded stent material is disposed in the body lumen and imposes a controlled, e.g., minimal, biological effect on the body at a cellular level. On the other hand, the volume of the stent 20 and the stent material are selected to provide a desired mechanical strength, e.g., radial strength, for expansion of the stent 20 and for supporting the stent 20 in the expanded state for a required length of time t, e.g., about a month to about three months. The biodegradable stent 20 can prevent galvanic reactions between the stent and a body fluid or body tissue when the stent is in use.

Figure 3:
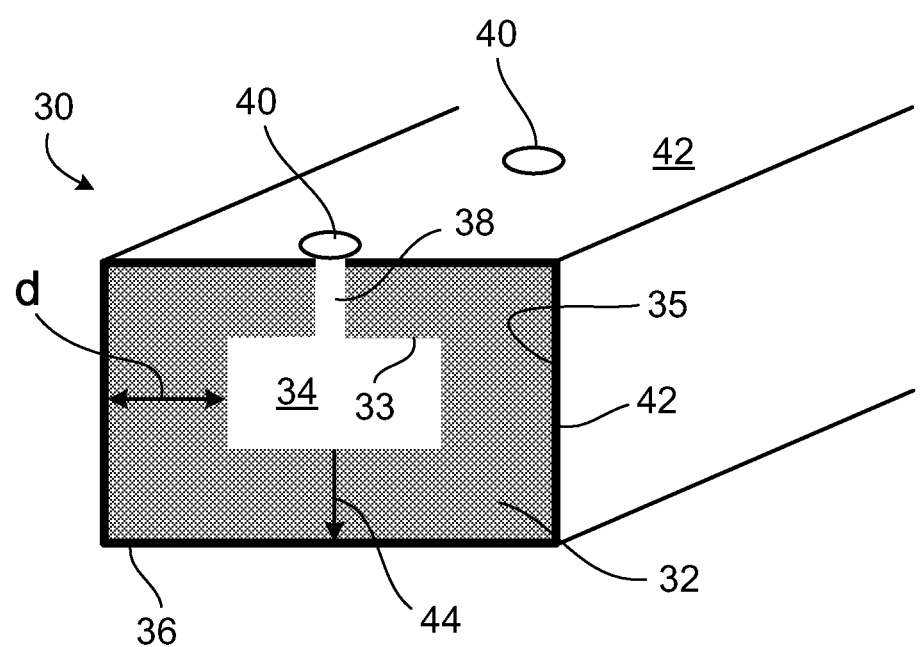
FIG. 3 is a schematic perspective view of a stent strut.

A first example of the bands 22 and the connectors 24 of the stent 20 having the features described above is shown in FIG. 3. A hollow stent strut 30 (components of the bands and the connectors) includes an inner layer 32 having an interior surface 33 surrounding a hollow interior 34 and an outer layer 36 on an exterior surface 35 of the inner layer 32. The hollow interior 34 is connected to the exterior of the strut 30 through pathways 38 in the inner and outer layers 32, 36 (not all shown), and ports 40 in the outer layer 36. In use, the body fluid contacts both an external surface 42 of the outer layer 36 and the interior surface 33 of the inner layer 32 and the strut 30 corrodes from both the inside and the outside. Materials in the inner and the outer layers 32, 36 are selected so that the outer layer 36 supports more stiffness of the strut 30 and corrodes much more slowly than the inner layer 32. In some embodiments, the strut 30 corrodes in an inside-out manner, i.e., substantially from the hollow interior 34, e.g., for about one month, before the second layer 36 is corroded to expose the exterior surface 35 of the first layer 32 to the body fluid. During this time t, the mechanical strength of the strut 30 is substantially maintained. After the exposure of the exterior surface 35, the corrosion of the strut 30 accelerates.

The inner layer 32 can include a metal that has an increasing density from the interior surface 33 to the exterior surface 35 along a radial direction 44. The low density portion of the inner layer 32 corrodes earlier and also faster than the high density portion, which further facilitates corroding the strut inside-out and maintaining the mechanical strength of the strut. The metal can be nanoporous metal foams having a thickness d of about 100 nm to about 50 microns. The diameters of the pores in the porous metal foams can be about 1 nm to about 5 nm. The metal foam can provide a mechanical strength similar to a bulk material having a similar thickness, while keeping the total volume of the stent material low. The nanoporous metal foams can be a three-dimensional network of high-strength or ultra-high-strength nanocolumns or nanowires, and can be highly porous. For example, the nanoporous metal foams include about 5%, 10%, 15%, and/or up to about 20%, 25% pores by volume. A similar volume of the stent material is reduced in comparison with the bulk material. The porous structure of the foams provides a large surface area for the body fluid to contact the foams and the corrosion can be accelerated.

Suitable metal for use in the inner layer 32 can include iron, magnesium, their alloys, or other biodegradable metals. Suitable material for use in the outer layer 36 can be a metal that corrodes more slowly than the metal in the inner layer 32. For example, when the inner layer 32 includes magnesium, the outer layer 36 can include iron. The outer layer 36 can also be a biodegradable polymeric coating, for example, a PLGA coating or a PLA coating. In some embodiments, additional particles, such as metal particles or electroconductive polypyrole nanoparticles, can be disposed in the biodegradable polymeric coating to further reduce the corrosion rate and/or the mechanical strength of the outer layer 36. The thickness of the outer layer 36 can be chosen so that the outer layer 36 is substantially fully corroded before, at the same time as, or after the inner layer 32 is substantially fully corroded. Because the inner layer 32 is corroded inside-out and can be independent of the corrosion of the outer layer 36, the outer layer 36 can have a relatively thin thickness and low corrosion rate to reduce the total volume of the stent material.

The strut 30 can carry a drug in the outer layer 36 that elutes when in contact with the body fluid. In some embodiments, the drug can elute at a rate similar to the corrosion rate of the outer layer 36 and can last, for example, about a month. The length of time t before the outer layer 36 is corroded away and for the elution of the drug can be controlled by the thickness and/or corrosion rate of the layer 36. In some embodiments, the inner layer 32 can also carry a drug, for example, in the pores of the porous foams. The drug in the inner layer 32 can have a higher elution rate than the elution rate of the drug in the outer layer 36.

In some embodiments, the strut 30 can contain radiopaque particles (not shown), such as gold nanoparticles, in the hollow interior 34. For example, a gold nanoparticle layer can be formed on the interior surface 33 of the inner layer 32 to assist visualization of the stent at different functional stages, e.g., delivery or corrosion. In some embodiments, the radiopaque particles can be co-deposited with metal particles that form the inner layer 32 using, for example, the Mantis technique (discussed below).

The dimensions of the ports 40, the pathways 38, and the hollow interior 34 can also affect the time length t during which the stent is mechanically supported by the outer layer 36. For example, small diameters of the ports 40 and pathways 38 can provide a long time length t. Each port 40 can have a diameter of about 0.5 micrometer to about 10 micrometers; the diameter of each pathway 38 can be about 0.5 micrometer to about 10 micrometers; and the hollow interior 34 can have in inner diameter of about 0.5 micrometer to about 50 micrometers. In other embodiments, the ports 40 and the pathways 38 can be in the form of a continuous trench (not shown) indented from the surface 42 of the outer layer 36 and in the inner and outer layers 32, 36. The trench structure can allow the body fluid to reach the hollow interior 34 quickly and accelerates the corrosion. In still other embodiments, the ports 40 and/or the trench can be sealed by weak spots (FIG. 4) in the outer layer 36. In use, the inner layer 32 of the strut 30 does not start corroding until the weak spots are corroded away and the time length t can be extended. Other configurations and dimensions of the portions of the strut 30 can be used for obtaining a desired time length t, mechanical strength, drug elution profile, and/or corrosion rate of the strut.

Figure 4:
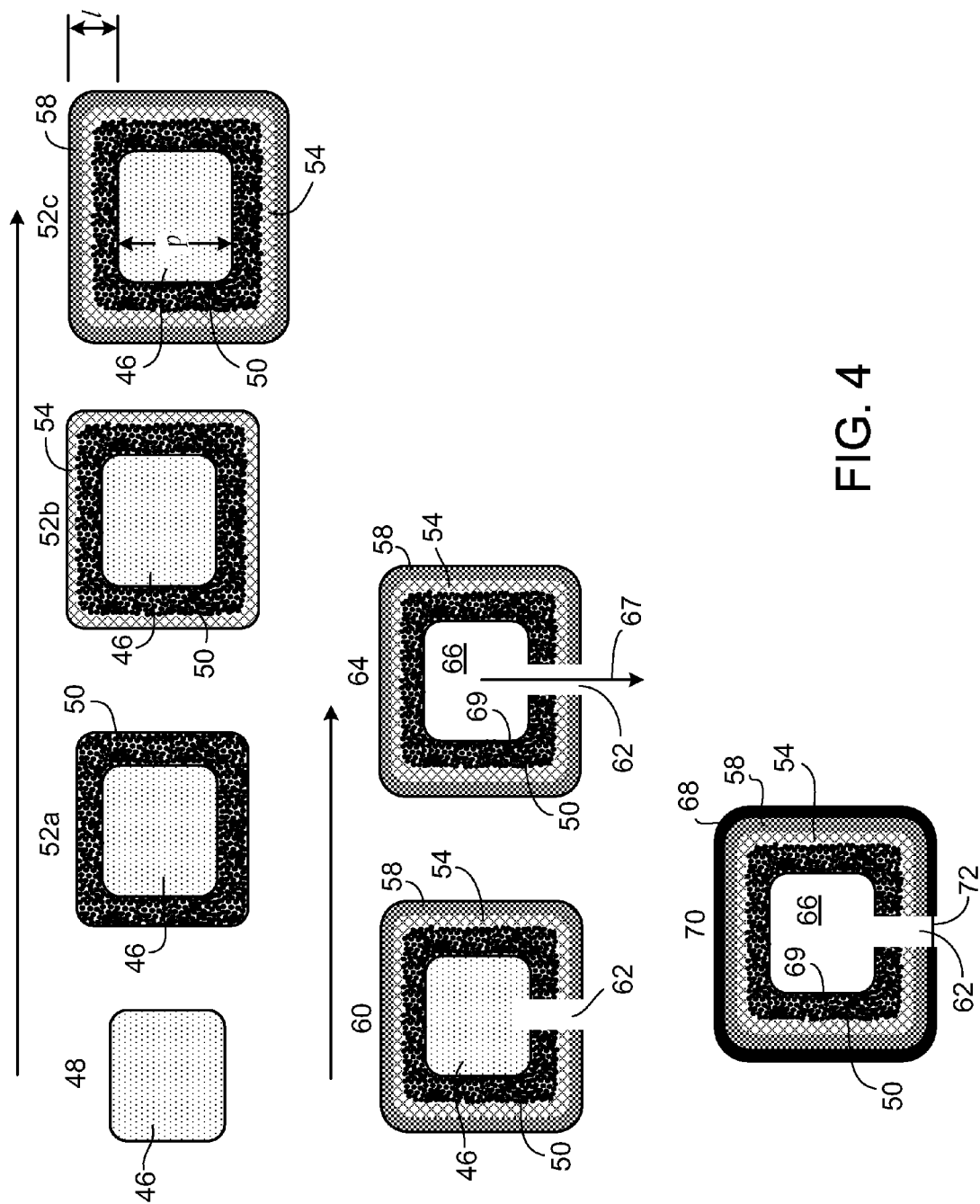
FIG. 4 is a schematic diagram of a method of making a stent strut.

FIG. 4 shows an example of making the stent strut 30. A thin polymer stent template 46 is provided (48), for example, by micro-molding. Information about the micro-molding technology is available, for example, from Sovrin Plastics at Slough, England. The dimensions of the template 46 can be selected based on the dimensions of the hollow interior (e.g., hollow interior 34 of FIG. 3) to be formed in the strut. Nanoporous metal networks 50, 54, 58 are sequentially formed (52*a*-52*c*) on the molded stent template 46 using, for example, a nano-cluster deposition system (IFC Medical or Mantis (UK)). During the deposition process, nanosized metal particles, e.g., iron particles, carrying charges are accelerated towards the template 46 under a bias voltage. When reaching the template 46, the particles collide with each other and with the template 46, and can partly melt, depending on their velocities. The nanoporous networks 50, 54, 58 are formed by the deposited particles. The Mantis technique is also discussed in U.S. provisional application No. 60/857,849 and U.S. application publication No. US 2008-0147177.

Different porosities of the nanoporous networks 50, 54, 58 can be obtained using particles having different sizes and by controlling the bias voltage at which these particles are deposited. Generally, larger particles and/or lower bias voltages create networks having higher porosities with larger pores. In the example shown in FIG. 4, the bias voltages used in steps 52a, 52b, 52c increase from low to high and the networks 50, 54, 58 are created with decreased porosity and pore sizes. In some embodiments, the networks 50, 54, 58 having different porosities can be formed continuously using the same metal particles by changing the bias voltages continuously. The overall porosity of the networks 50, 54, 58 can increase continuously from the template 46 to the exterior network 58. In some embodiments, the networks 50, 54, 58 can be formed in separate steps. In different steps, the particle sizes can be changed in addition to the change of the bias voltages.

The sizes of the metal particles used for the deposition can be between about 1 nm and about 1 micrometer. The bias voltage can be about 500 V to about 1000V, or even higher than 3000 V. In some implementations, the deposition rate is in the order of angstroms per second and it takes about 5 minutes to about 10 minutes of deposition time to form the networks 50, 54, 58 having a total thickness/of about 30 microns on when the template 46 has a thickness p of about 60 microns.

A pathway 62 is formed (60), e.g., by laser ablation, in the networks 50, 54, 58 so that the template 46 is exposed to the exterior of the network 58. The template 46 is removed (64) from the interior of the network 50 by, for example, calcination, plasma etching, or chemical dissolution (along the direction 67). A hollow interior 66 that is surrounded by the network 50 is formed and is connected to the exterior of the networks through the pathway 62.

A biodegradable polymeric coating 68, such as PLGA, is formed (70) on the network 58 by a coating process, for example, spraying, dipcoating, or plasma coating. A drug or additional particles, such as electroconductive polypyrole nanoparticles, can be co-deposited with the polymer coating 68. In some embodiments, one or more of a coating material for the polymeric coating 68, the drug, and the nanoparticles can be deposited simultaneously or in a sequential manner in various orders. The manner of the deposition of the drug and the nanoparticles relative to the coating material can affect the timing of the drug elution and the strength and corrosion of the stent. For example, when the drug is deposited after the deposition of the polymeric coating 68, the drug can elute from its initial contact with the body fluid once the stent is delivered; when the drug is deposited before the deposition of the polymer coating 68, the drug can elute through the pores of the networks 50, 54, 58 initially and also later from the pores formed in the corroded polymer layer 68.

The opening of the pathway 62 to the exterior can be masked during the deposition of the polymer coating 68 so that the pathway 62 does not become sealed or blocked. When no mask is used, a thin layer 72 continuous of the polymer coating can be formed over the pathway 62 and seals the pathway. The thin layer 72 can include a material the same as or different from the coating material in the polymer coating 68 and can have a thickness smaller than a thickness of the polymer coating 68. For example, the thin layer 72 can have a thickness that is 1/10 to about 1/2 of the average thickness of the polymer coating 68. Penetration of the thin layer 72 can be established sooner than the penetration of the polymer coating 68, forming a port for the body fluid to enter the hollow interior 66 through the pathway 62.

In other embodiments, one or more drugs can be loaded into the networks 50, 54, 58, simultaneous to or after the formation of the networks and prior to the formation of the polymer coating 68. Methods suitable for the loading of the drugs include co-deposition of the metal nanoparticles and the drug component. For example, the co-deposition can be performed by evaporating the drug in a heated boat at a temperature of about 80 Celsius degrees to about 120 Celsius degrees and forming condensation on the growing metal matrix. The drug/metal ratio can be changed by changing the metal deposition speed versus the evaporation speed of the drug. A thickness of the networks containing drugs can be controlled by deposition time. In some embodiments, paclitaxel (Ptx) and tantalum (Ta) co-deposition are co-deposited for about 20 to about 40 minutes. In some embodiments, the nanoparticles have a size of, e.g., about 50 nm. Adhesion of the coating formed by the metal nanoparticles and the drug component can be enhanced by cleaning the stent surface of foreign matter prior to depositing, e.g., using isopropyl alcohol (IPA) or plasma. The drugs in the networks 50, 54, 58 can be protected by the polymer coating 68 during delivery of the stent and are released after the thin layer 72 or the polymer coating 68 penetrates.

In still other embodiments, a radiopaque material, such as gold nanoparticles, can be incorporated in the template 46 in step 48, for example, by mixing the polymer material and the gold nanoparticles prior to the micromolding. The gold nanoparticles remain in the hollow interior 66 when the polymer template 46 is removed in step 64 and form a radiopaque layer on an interior surface 69 of the network 50. The radiopaque layer does not dissolve until the end of the stent corrosion and can facilitate tracking of the stent delivery and performance. For example, whether the stent has fully degraded can be observed using an X-ray. The gold nanoparticles have small sizes to enable removal of the particles by the body.

A second example of the bands 22 and connectors 24 of the stent 20 having the features described above is shown in FIG. 5. A strut 80 has a polymer core 82 enclosed by metal shell 84. The metal shell 84 can have high mechanical strength and a high Young's modulus, and can determine the mechanical performance of the strut 80. The polymer core 82 has relatively low mechanical strength and a low Young's modulus. However, when the metal shell 84 breaks unexpectedly, the polymer core 82 can also provide mechanical support for the strut. In use, the metal shell 84 degrades at a low rate for about 30 to about 90 days while substantially keeping the mechanical strength of the stent prior to substantially exposing the polymer core 82 to the body fluid. For example, the mechanical strength of the stent decreases by about 10% to about 99% after 30 to 90 days. In particular, mechanical strength of a stent having an iron metal shell 84 decreases less than the mechanical strength of a stent having a magnesium metal shell 84, after the same amount of time. The length of time t before the metal shell 84 substantially degrades and the mechanical strength of the strut 80 can be controlled by the material used for and the thickness of the metal shell 84, and the thickness ratio of the shell 84 to the core 82. In some embodiments, the metal shell 84 can have a thickness of about 1 micron to about 40 microns, about 10 microns to about 40 microns, or about 20 microns to about 40 microns. The dimensions of the cross-section of the strut 80 is about 50 microns by 50 microns. Once substantially exposed, the polymer core 82, and therefore, the strut 80, quickly degrades, for example, in about 20 days to about 90 days.

The polymer core 82 can include polylactide (PLA) or PLGA, and optionally a drug, that are, for example, micro-injection-molded or laser-cut. In some embodiments, the metal shell 84 includes fine, e.g., ultra-fine, grains of magnesium, iron, magnesium alloy, iron alloy, or other biodegradable metals, particles deposited using, for example, physical vapor deposition (PVD) or pulsed laser deposition (PLD). In the PVD process, a relatively high sputter rate can be achieved using a hollow cathode. The PLD process can reduce the thermal impact on the polymer core 82. The grains form of the metal shell 84 can enable the strut 80 to have a good ductility.

In some embodiments, the metal shell 84 substantially seals the polymer core 82 and the drug contained in the polymer core 82 does not release until one or more pores or channels are formed in the degrading metal shell 84 and the body fluid contacts the polymer core 82 through the pores or channels. The starting time of the drug release can be controlled by the parameters, such as the corrosion rate and the thickness, of the metal shell 84. The releasing rate and releasing profile of the drug can be adjusted by selecting the density of the drug in the polymer core 82 and the other related parameters, such as the sizes and the corrosion rate of, or the materials in the polymer core 82.

Figure 6:
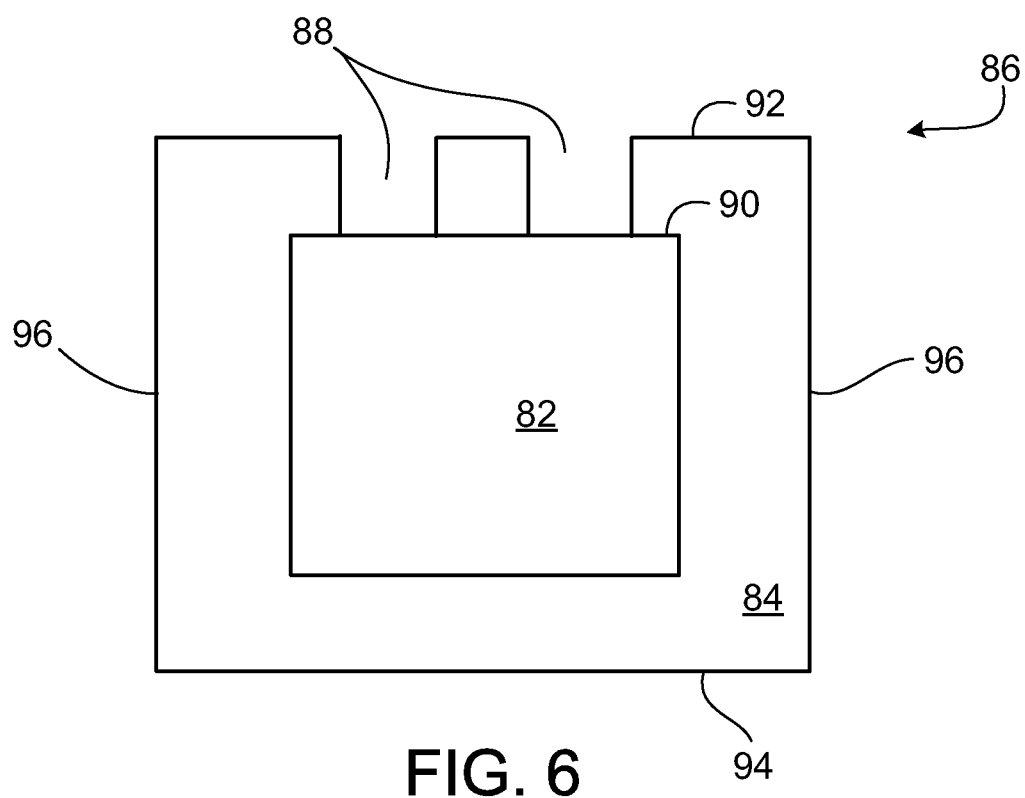

In the example shown in FIG. 6, the metal shell 84 of a strut 86 includes pores 88 that exposes a surface 90 of the polymer core 82 to the exterior of the metal shell 84. In use, the drug in the polymer core 82 is exposed to the body fluid prior to substantial corrosion of the metal shell 84 and can be released at the early stage of the stent delivery. The pores 88 can have regular or irregular shapes and can have an average diameter of about 1 micron to about 20 microns. The pores 88 can be formed during or after the formation of the metal shell 84. For example, colloidal lithography can be used by applying a mask to the polymer core 82 during the deposition of the metal shell to form the pores 88 at masked locations. In another example, the strut 86 can be formed by applying laser beams to the strut 80 to create pores 88 at intended locations (laser ablation). Other methods, such as etching can also be used. The pores 88 can be located on one or more surfaces of the strut 86, for example, abluminal surface 92, adluminal surface 94, and/or cut surfaces 96 of the strut. The pores 88 on the one or more of the surfaces can have a uniform density and/or average size. In some embodiments, the pores 88 on one or more particular regions of a surface or a particular surface among all surfaces have a larger density or average size than the other regions or surfaces to release the drug at a high rate. Various configurations can used for different drug release profiles and corrosion time controls.

Figure 5:
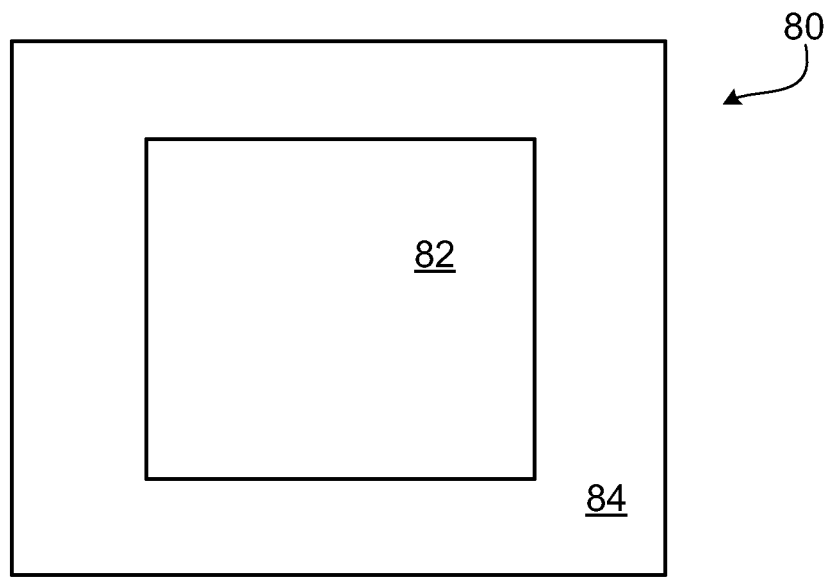
FIGS. 5 and 6 are schematic cross-sectional views of stent struts.
Figure 7:
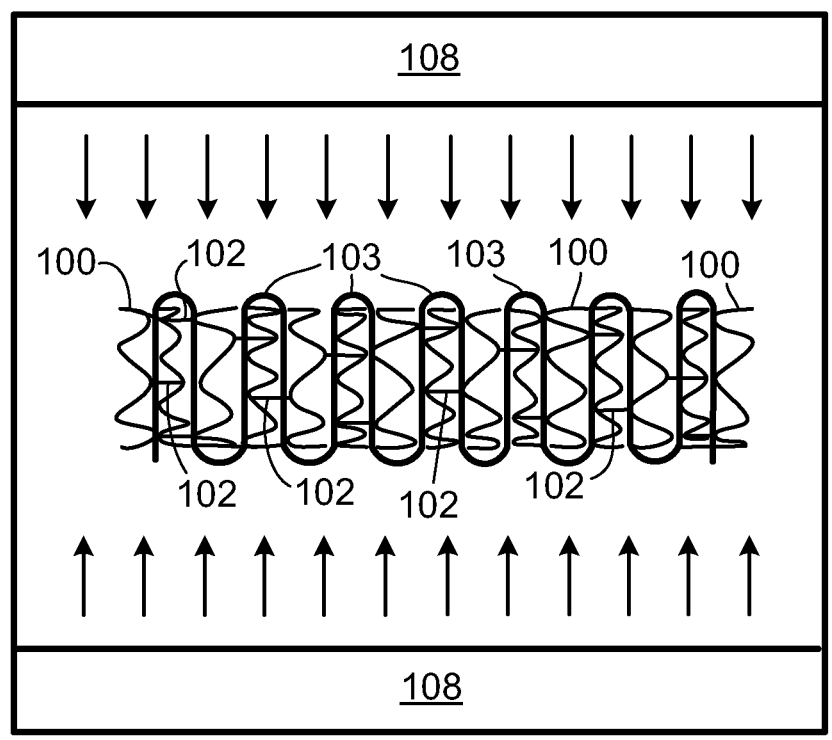
FIG. 7 is a schematic diagram of a setting for making a stent.

The strut 80 of FIG. 5 or the strut 86 of FIG. 6 can be a portion of radial bands 100 and/or longitudinal connectors 102 of a stent 104 shown in FIG. 7. The radial bands 100 is self-expandable or balloon-expandable and has a high Young's modulus to provide the strength to support the radial expansion of the stent. The longitudinal connectors 102 provides connections to the bands 100 and longitudinal flexibility to the stent 104. In some embodiments, the stent 104 has metal shells (such as the metal shell 84 of FIGS. 5 and 6) covering only the radial bands 100 to provide the bands with the desired mechanical strength. The uncovered polymer longitudinal connectors 102 can provide a high longitudinal flexibility and a high fatigue resistance. For example, the stent 104 can be readily bent at locations along the longitudinal axis and can fit to the tortuous body lumen.

In the example shown in FIG. 7, the radial bands 100 made of a polymer material can be selectively coated with the metal shell by masking the longitudinal connectors 102 using a ring mask 103, which is positioned around segments of the stent connectors 102. Metal, e.g., iron, particles are sputtered from targets 108 using PVD, e.g., magnetron sputtering with a hollow cathode, or PLD. Other suitable masks and deposition methods can also be used to effectively coat the radial bands 100 without covering the connectors 102.

Figure 8:
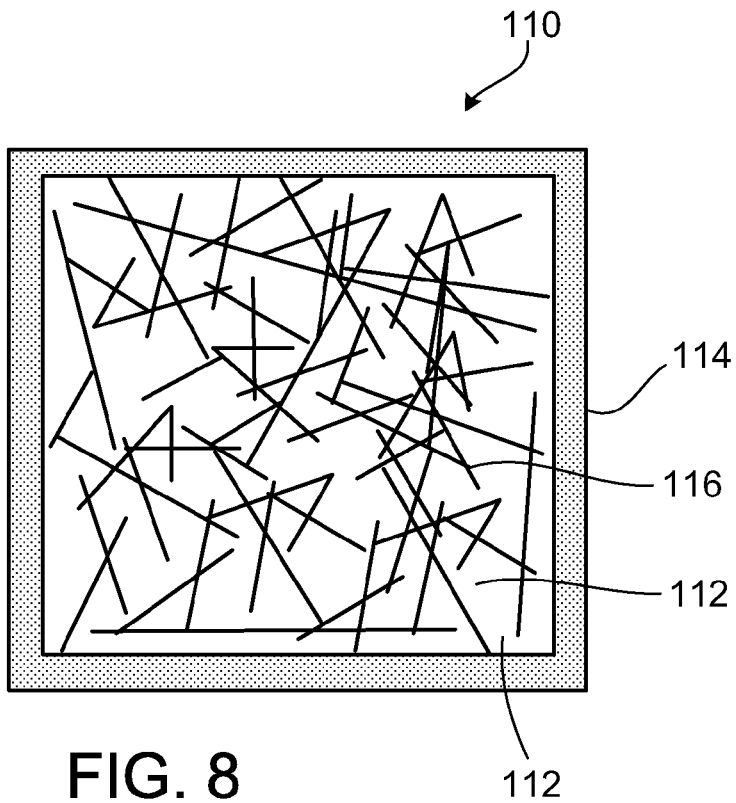
FIGS. 8 and 9 are schematic cross-sectional views of stent struts.
Figure 9:
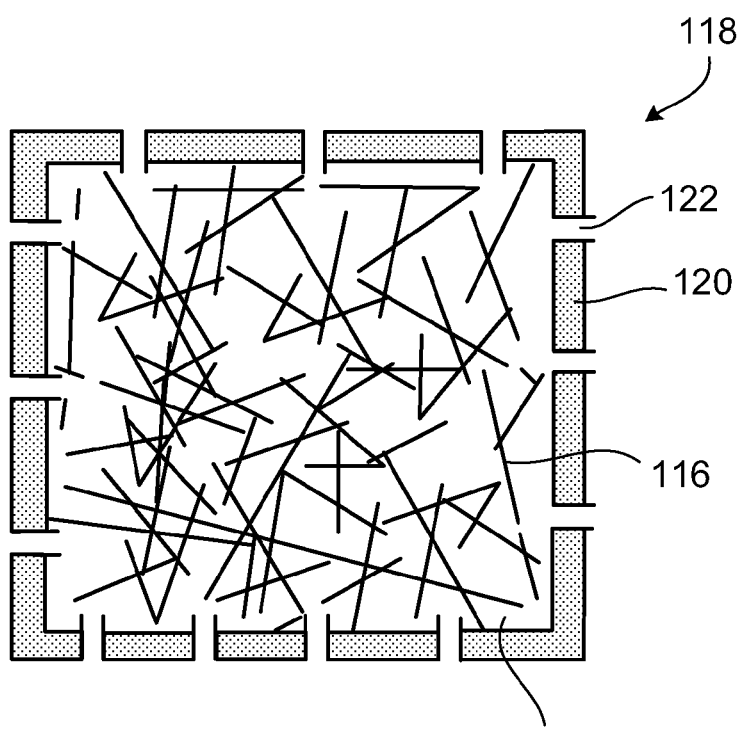

A third example of the bands 22 and connectors 24 of the stent 20 having the features described above is shown in FIG. 8. A strut 110 includes a metal, e.g., iron, shell 114 encapsulating a collagen matrix 112 carrying metal oxide, e.g., iron oxide (FeOx), particles 116. In use, the strut 110 undergoes a slow degradation of the metal shell, during which mechanical strength of the strut 110 is substantially maintained, followed by a rapid degradation of the collagen matrix 112 with the metal oxide particles 116. The metal oxide particles 116 can increase the mechanical strength of the collagen matrix so that the strut 110 can remain mechanically strong even after the degradation of the metal shell 114.

A composite of a collagen material and the metal particles can be pre-made for making of the collagen matrix 112 containing the metal particles 116 by, for example, wet chemistry formulations. The metal particles can be incorporated into an anionic collagen prepared in an acidic environment. In some embodiments, a neutral collagen solution can be used. The metal particles can also be incorporated into the collagen by mechanical mixing. Methods of making the composition of the collagen with incorporated metal particles are discussed by Goissis et al., $10^{th}$ international symposium on electrets (1999), pages 229-232; Goissis et al., Revista Brasileira de Engenharia Biomedica 15 (1999), pages 55-61; Berry et al., J. Phys. D: Appl. Phys. 36 (2003), R198-R206; Gupta et al., Biomaterials 26 (2005), pages 3995-4021; McLean et al., applied and environmental microbiology 56 (1990), pages 3671-3677; and Wood et al., Biochem. J. 75 (1960), pages 588-598. Synthesis of collagen is described by Gibson et al., J. of Cell Biology 99, 208-216 (1984). Collagen gel used for delivery and tissue engineering is described by Wallace et al., Advanced Drug Delivery Reviews 55, 1631-1649 (2003). Behavior of gelatin gels and their biomedical use are described by Lou et al., J. Biomater. Appl. 14, 184 (1999).

The collagen-metal oxide particle composition can be extruded or injection-molded into a desired shape for the strut 110. In some embodiments, laser cutting can also be used. The iron shell 114 having a desired thickness can be electroplated onto the collagen matrix 112. Other methods, such as PLD or PVD, electroless plating, metal fuse, can also be used. The iron shell 114 can have a thickness of about 100 nm to about several microns, e.g., about 200 nm to about 5000 nm. Suitable methods or control parameters in each method can be chosen for forming the iron shell having a particular thickness. For example, control of electroless plating parameters for iron deposition is described in Dinderman et al., Chem. Mater. 18, 4361-4368 (2006). Metal fuse to provide metal/polymer hybrids is developed, for example, by E.I. du Pont de Nemours and Company (DuPont). Metal fuse is also described in Day, Advanced Materials and Processes, 25-27 (April 2008). Other methods also include the methods for forming nano-coating developed by Integran Technologies Inc. (Pittsburg, Pa.).

In another embodiment, a strut 118 can include a metal mesh 120 surrounding the collagen matrix 124. The collagen matrix 124 can optionally include metal or metal oxide particles similar to the collagen matrix 112 of FIG. 8. In some embodiments, the collagen matrix 112 can be free of any metal or metal oxide particles. The collagen matrix 124 and the optional incorporation of the metal or metal oxide particles can be done in a way similar to the making of the collagen-metal oxide particle composition described previously. The mesh 120 can be deposited using a method similar to the deposition of the metal shell 114 of FIG. 8, with an addition of one or more masks covering portions of the collagen matrix 124 where openings 122 are to be created. Alternatively, the openings 122 of the mesh shell 114 can also be created by laser ablation or other methods, similar to the creation of the openings 88 of FIG. 6. The openings 122 can have an average diameter of about 1/20 to about 1/10 of a thickness of the strut 118. The thickness of the strut 118 can be selected based on, e.g., the material used for the strut, e.g., magnesium or iron, and the desired degradation profile. In some embodiments, the opening 122 can have an average diameter of about 0.5 micrometer or about 10 micrometers. The strut 118 can have properties, such as mechanical strength or corrosion rate and duration, similar to the strut 110.

In use, metal-complex particles, e.g., Fe complexations, can be produced in vitro by the reactions among the metal in the mesh shell 114, the collagen in the collagen matrix 126, and the body fluid. The produced metal-complex particles can be incorporated in the collagen matrix 124 to increase the mechanical strength of the collagen matrix, without having the collagen matrix 124 made with the metal or metal oxide particles 116 incorporated. In particular, when an electrolyte solution (body fluid) contacts the collagen matrix 124 and the Fe at the interface of the two materials, the metallic Fe oxidizes to form $Fe^{2+}$ and $Fe^{3+}$ ions. The anionic collagen in the collagen matrix 124 can create an acidic environment by dissociation of carboxylic groups. In some embodiments, the collagen can also be functionalized by an amine, a hydroxyl, or a thiol group. The Fe cations form complexes/salts with the dissociated $COO^-$ groups. In some embodiments, the collagen in the collagen matrix can have a low molecular weight, for example, of about 40 KDaltons to about 60 KDaltons and can be soluble or in the form of a gel. The formed iron complexation and the collagen matrix 124 can together be soluble. Iron complexation formation is also discussed by Shears et al., J. Food Sci. Techn. 22 (1987), pages 265-272 and Yu et al., Chinese Journal of Polymer Science 8 (1990), pages 247-252. The solubility of the collagen is discussed by Wolf et al., IUFoST 20060929 (2006).

Other than collagen, other polymers that have functional groups capable of forming complexes with iron can also be used in replacement of or together with the collagen in the collagen matrix 124. Examples of the other polymers can include polyelectrolytes, e.g., poly(styrenesulfonate), hydride ligands, halide ligands, polysaccharides (chitosan), proteins, polyvinyl alcohol (PVA), and many others. The collagen or the polymers can form complexes with the irons and can act as chelators in the collagen or polymer matrix. The other polymers are also discussed by Phenrat et al., J. Nanopart. Res. 10 (2008), pages 795-814; and Nordlander et al., coordination chemistry reviews 172 (1998), pages 3-97. In addition, polymer or polymer blends, for example, poly(vinyl alcohol) (PVA), can be included in the collagen matrix, for example, to modify the thermal or elastic properties of the collagen matrix. Discussion of the polymer-collagen blend is provided by Lai et al., Korean-Australian Rheology Journal 19 (2007), pages 81-88.

The collagen or polymer matrix can also include one or more chelating agents, for example, sodium 4,5-dihydroxybenzene-1,3-disulfonate (Tiron), desferrioxamine (DFO), ethylenediaminetetraacetic acid (EDTA), and others. The chelating agents can be selected to facilitate control of the corrosion of the collagen or polymer matrix, for example, accelerating the corrosion or decreasing the speed of corrosion. Iron-chelating agents are described by Hershko et al., British Journal of Haematology 51, 251-260 (1982).

Figure 10:
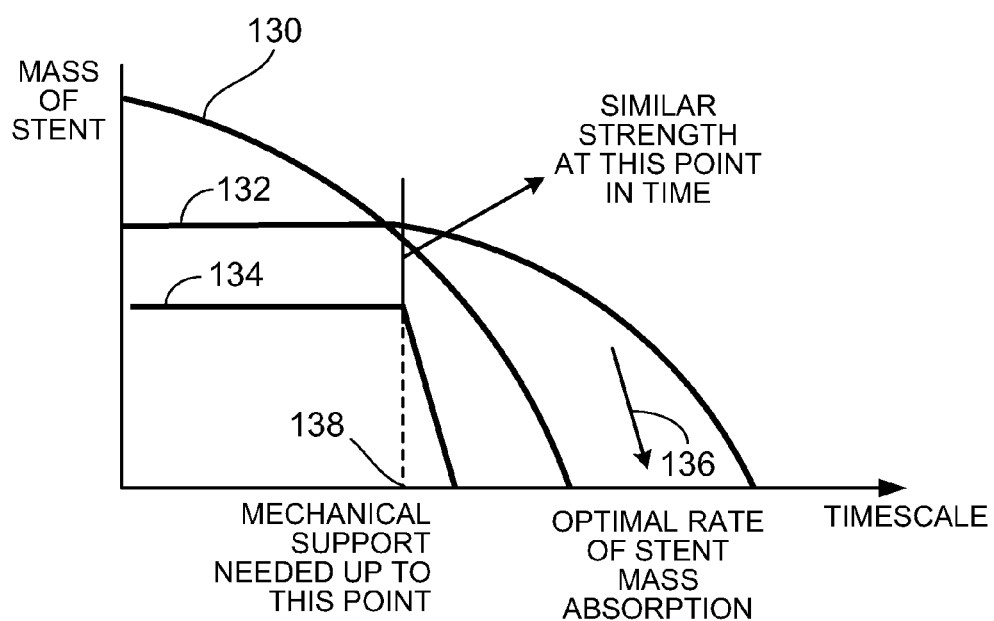
FIG. 10 is a plot of stent mass versus corrosion time for three different stents.

Referring to FIG. 10, a comparison of three stents having the same dimensions and made of different materials is provided. The relationships among the mass of each stent, mechanical strength of each stent, and the corrosion time are illustrated in the plot.

A first stent is made of bare iron and its performance corresponds to a curve 130. A second stent is made of a PLA shell surrounding a solid bare iron substrate and its performance is shown by a curve 132. A third stent is made of a PLA shell surrounding a iron foam having a hollow interior (e.g., the strut 30 of FIG. 3) and its performance is shown by a curve 134.

The first stent has the largest mass among all three stents, being about 4/3 times as large as the mass of the second stent and two times as large as the mass of the third stent. All three stents are capable of having proper mechanical strength until a desired time point 138, for example, 30-90 days after the delivery. The mass of the first stent decreases before reaching the time point 138, while the masses of the second and the third stents remain substantially the same until reaching the time point 138. After the time point 138, a slope of an arrow 136 shows a desired quick corrosion rate for the remaining of the stents. The first stent corrodes faster than the second stent, and both corrode more slowly than the desired quick corrosion rate. The third stent corrodes at a rate similar to the desired quick corrosion rate.

The terms "therapeutic agent", "pharmaceutically active agent", "pharmaceutically active material", "pharmaceutically active ingredient", "drug" and other related terms may be used interchangeably herein and include, but are not limited to, small organic molecules, peptides, oligopeptides, proteins, nucleic acids, oligonucleotides, genetic therapeutic agents, non-genetic therapeutic agents, vectors for delivery of genetic therapeutic agents, cells, and therapeutic agents identified as candidates for vascular treatment regimens, for example, as agents that reduce or inhibit restenosis. By small organic molecule is meant an organic molecule having 50 or fewer carbon atoms, and fewer than 100 non-hydrogen atoms in total.

Exemplary therapeutic agents include, e.g., anti-thrombogenic agents (e.g., heparin); anti-proliferative/anti-mitotic agents (e.g., paclitaxel, 5-fluorouracil, cisplatin, vinblastine, vincristine, inhibitors of smooth muscle cell proliferation (e.g., monoclonal antibodies), and thymidine kinase inhibitors); antioxidants; anti-inflammatory agents (e.g., dexamethasone, prednisolone, corticosterone); anesthetic agents (e.g., lidocaine, bupivacaine and ropivacaine); anti-coagulants; antibiotics (e.g., erythromycin, triclosan, cephalosporins, and aminoglycosides); agents that stimulate endothelial cell growth and/or attachment. Therapeutic agents can be nonionic, or they can be anionic and/or cationic in nature. Therapeutic agents can be used singularly, or in combination. Preferred therapeutic agents include inhibitors of restenosis (e.g., paclitaxel), anti-proliferative agents (e.g., cisplatin), and antibiotics (e.g., erythromycin). Additional examples of therapeutic agents are described in U.S. Published Patent Application No. 2005/0216074. In some embodiments, the drug can be incorporated within the porous regions in a polymer coating. Polymers for drug elution coatings are also disclosed in U.S. Published Patent Application No. 2005/019265A. A functional molecule, e.g., an organic, drug, polymer, protein, DNA, and similar material can be incorporated into groves, pits, void spaces, and other features of the stent.

Suitable polymers include, for example, polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics such as polystyrene and copolymers thereof with other vinyl monomers such as isobutylene, isoprene and butadiene, for example, styrene-isobutylene-styrene (SIBS), styrene-isoprene-styrene (SIS) copolymers, styrene-butadiene-styrene (SBS) copolymers, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenerated polyalkylenes including polytetrafluoroethylene, natural and synthetic rubbers including polyisoprene, polybutadiene, polyisobutylene and copolymers thereof with other vinyl monomers such as styrene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyiocyanates such that the devices become instantly lubricious when exposed to body fluids. In another preferred embodiment of the invention, the polymer is a copolymer of polylactic acid and polycaprolactone. Suitable polymers are discussed in U.S. Publication No. 2006/0038027.

In some embodiments, the polymer is capable of absorbing a substantial amount of drug solution. When applied as a coating on a medical device in accordance with the present invention, the dry polymer is typically on the order of from about 1 to about 50 microns thick. Very thin polymer coatings, e.g., of about 0.2-0.3 microns and much thicker coatings, e.g., more than 10 microns, are also possible. Multiple layers of polymer coating can be provided. Such multiple layers are of the same or different polymer materials.

Any stent described herein can be dyed or rendered radiopaque by addition of, e.g., radiopaque materials such as barium sulfate, platinum or gold, or by coating with a radiopaque material. The stent can include (e.g., be manufactured from) metallic materials, such as stainless steel (e.g., 316L, BioDur® 108 (UNS S29108), and 304L stainless steel, and an alloy including stainless steel and 5-60% by weight of one or more radiopaque elements (e.g., Pt, Ir, Au, W) (PERSS®) as described in US-2003-0018380-A1, US-2002-0144757-A1, and US-2003-0077200-A1), Nitinol (a nickel-titanium alloy), cobalt alloys such as Elgiloy, L605 alloys, MP35N, titanium, titanium alloys (e.g., Ti-6A1-4V, Ti-50Ta, Ti-10Ir), platinum, platinum alloys, niobium, niobium alloys (e.g., Nb-1Zr) Co-28Cr-6Mo, tantalum, and tantalum alloys. Other examples of materials are described in commonly assigned U.S. application Ser. No. 10/672,891, filed Sep. 26, 2003; and U.S. application Ser. No. 11/035,316, filed Jan. 3, 2005. Other materials include elastic biocompatible metal such as a superelastic or pseudo-elastic metal alloy, as described, for example, in Schetsky, L. McDonald, "Shape Memory Alloys", Encyclopedia of Chemical Technology (3rd ed.), John Wiley & Sons, 1982, vol. 20. pp. 726-736; and commonly assigned U.S. application Ser. No. 10/346,487, filed Jan. 17, 2003.

The stents described herein can be configured for vascular, e.g., coronary and peripheral vasculature or non-vascular lumens. For example, they can be configured for use in the esophagus or the prostate. Other lumens include biliary lumens, hepatic lumens, pancreatic lumens, urethral lumens.

The stent can be of a desired shape and size (e.g., coronary stents, aortic stents, peripheral vascular stents, gastrointestinal stents, urology stents, tracheal/bronchial stents, and neurology stents). Depending on the application, the stent can have a diameter of between, e.g., about 1 mm to about 46 mm. In certain embodiments, a coronary stent can have an expanded diameter of from about 2 mm to about 6 mm. In some embodiments, a peripheral stent can have an expanded diameter of from about 4 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. The stent can be balloon-expandable, self-expandable, or a combination of both (e.g., see U.S. Pat. No. 6,290,721).

All publications, patent applications, patents, and other references mentioned herein are incorporated by reference herein in their entirety.

Still further embodiments are in the following claims.

What is claimed is:

1. A bio-erodible implantable endoprosthesis comprising a member that includes (a) a core having a surface, and (b) a bio-erodible metal on a least a portion of the surface of the core, wherein the bio-erodible metal erodes more slowly than the core and includes openings through which physiological fluids can access the core upon implantation, wherein the bio-erodible metal is in the form of a mesh.

2. The endoprosthesis of claim 1 in which the bio-erodible metal has a thickness of about 20 microns to about 40 microns.

3. The endoprosthesis of claim 1 in which the member is a strut.

4. The endoprosthesis of claim 1 in which the endoprosthesis is a stent.

5. A bio-erodible endoprosthesis comprising:
radially expandable members each including a metal shell covering at least a portion of a core that is mechanically less strong than the metal shell to provide radial mechanical strength when the member is expanded, and
longitudinal connectors, each connecting two radially expandable members along a longitudinal axis of the endoprosthesis, wherein each longitudinal connector includes the core without the metal shell to provide flexibility along the longitudinal axis.

6. A bio-erodible implantable endoprosthesis comprising a member that includes (a) a hollow core, (b) a porous bio-erodible metal surrounding the core and having a surface, wherein the density of the porous bio-erodible metal decreases in the thickness direction from the surface to the core, and (c) a bio-erodible layer covering at least a portion of the surface of the bio-erodible metal that provides openings through which physiological fluids can access the porous bio-erodible metal, the core, or both upon implantation.

7. The endoprosthesis of claim 6 in which the bio-erodible layer comprises a bio-erodible polymer.

8. The endoprosthesis of claim 7 in which the bio-erodible polymer is PLA, PLGA, or a combination thereof.

9. The endoprosthesis of claim 7 in which the bio-erodible polymer includes electroconductive particles.

10. The endoprosthesis of claim 9 in which the electroconductive particles comprises electroconductive polymer particles.

11. The endoprosthesis of claim 6 in which the porosity of the porous bio-erodible metal increases in the thickness direction from the surface to the core.

12. The endoprosthesis of claim 6 in which the porous bio-erodible metal has a thickness of about 30 microns and the hollow core has a diameter of about 60 microns.

13. The endoprosthesis of claim 6 in which the bio-erodible metal includes a channel in communication with the hollow core and covered by the bio-erodible layer.

14. The endoprosthesis of claim 6 in which the bio-erodible layer is less erodible than the bio-erodible metal.

15. The endoprosthesis of claim 6 in which the bio-erodible layer includes a drug.

16. The endoprosthesis of claim 6 in which the bio-erodible layer is porous.

17. The endoprosthesis of claim 6 in which the bio-erodible layer is provided with channels.

18. The endoprosthesis of claim 6 in which the core includes radiopaque particles.

19. The endoprosthesis of claim 6 in which the bio-erodible metal comprises iron or an alloy thereof.

20. The endoprosthesis of claim 6 in which the bio-erodible metal comprises magnesium or an alloy thereof.

21. The endoprosthesis of claim 6 in which the bio-erodible metal pores are nano-sized pores.

22. The endoprosthesis of claim 6 in which the member is a strut.

23. The endoprosthesis of claim 6 in which the member is a connector.

24. The endoprosthesis of claim 6 in which the endoprosthesis is a stent.

* * * * *

UNITED STATES PATENT AND TRADEMARK OFFICE
CERTIFICATE OF CORRECTION

| | | |
|---|---|---|
| PATENT NO. | : 8,834,560 B2 | Page 1 of 1 |
| APPLICATION NO. | : 13/051496 | |
| DATED | : September 16, 2014 | |
| INVENTOR(S) | : Jan Weber et al. | |

It is certified that error appears in the above-identified patent and that said Letters Patent is hereby corrected as shown below:

On the Title Page

Page 1 Col. 2 In Abstract Line 3, Delete "on a least a portion" and insert --on at least a portion--, therefor.

Page 2 Col 1 Line 1, Delete "Chemisty"," and insert --Chemistry",--, therefor.

Page 2 Col 2 Line 53, Delete "Envionmental" and insert --Environmental--, therefor.

Page 3 Col 1 Line 59, Delete "Appln." and insert --Appl.--, therefor.

Page 3 Col 2 Line 3, Delete "Appln." and insert --Appl.--, therefor.

Page 3 Col. 2 Line 50, Delete "polyeletrolyte" and insert --polyelectrolyte--, therefor.

Page 3 Col. 2 Line 54, Delete "murin" and insert --murine--, therefor.

Page 3 Col. 2 Line 55, Delete ""Nano-identation" and insert --"Nano-indentation--, therefor.

In the Claims

Col. 14 Claim 1 Line 40, Delete "on a least a portion" and insert --on at least a portion--, therefor.

Signed and Sealed this
Twenty-third Day of December, 2014

Michelle K. Lee
*Deputy Director of the United States Patent and Trademark Office*